United States Patent [19]
Kredovski

[11] Patent Number: 6,162,251
[45] Date of Patent: Dec. 19, 2000

[54] SALINE IMPLANT HAVING SINGLE VALVE WITH PRIMARY AND SECONDARY CLOSURES

[75] Inventor: Kenneth C. Kredovski, Minneapolis, Minn.

[73] Assignee: Novamed Medical Products Manufacturing, Inc., Minneapolis, Minn.

[21] Appl. No.: 09/318,036

[22] Filed: May 25, 1999

[51] Int. Cl.⁷ ................................................. A61F 2/02
[52] U.S. Cl. .................. 623/8; 623/23.67; 623/23.68; 623/11.11
[58] Field of Search ..................... 623/7, 8, 23.67, 623/23.68, 11.11; 604/167, 256, 169; 137/1; 251/351, 352

[56] References Cited

U.S. PATENT DOCUMENTS

| | | | |
|---|---|---|---|
| 3,599,681 | 8/1971 | Hall | 251/352 |
| 4,433,440 | 2/1984 | Cohen | 623/8 |
| 4,643,733 | 2/1987 | Becker | 623/8 |
| 4,685,447 | 8/1987 | Iverson et al. | 623/8 |
| 5,456,716 | 10/1995 | Iversen et al. | 623/8 |
| 5,507,808 | 4/1996 | Becker | 623/8 |
| 5,865,807 | 2/1999 | Blake, III | 604/167 |
| 6,079,432 | 6/2000 | Paradis | 604/167 |

*Primary Examiner*—David J. Isabella

[57] ABSTRACT

An implant that includes an envelope, a saline based fill material in the envelope, and a single valve. The envelope is formed by a mandrel dipping process and includes an opening formed by a support rod for the mandrel. To remove the envelope from the mandrel, the opening is stretched over the mandrel. This opening, a natural port, is sealed by a single valve structure. The valve structure includes the valve through which the saline based fill material is introduced. The valve is two piece, and the two pieces mechanically interlock to bias and draw a diaphragm tightly against a valve seat, which provides a primary resilient closure for the valve. The valve further includes a secondary resilient closure where two confronting faces form a slit through which a filling tube is inserted and where end portions of the two confronting faces are bonded to each other to minimize the chances of the slit tearing at its ends.

21 Claims, 9 Drawing Sheets

SALINE IMPLANT HAVING SINGLE VALVE WITH PRIMARY AND SECONDARY CLOSURES

BACKGROUND

The present invention relates generally to an implant for the body, particularly to an implant having a saline based fill material, and specifically to such an implant having, except for a single opening, an integral envelope.

A "safe" implant may be an impractical goal. A "safer" implant is attainable. A safer implant may be one that 1) is simple, 2) has a minimum number of parts, and 3) has the least possible number of openings. A safer implant may have other characteristics as well such as having a biocompatible fill material. One example of a biocompatible fill material is saline.

SUMMARY OF THE INVENTION

A feature of the invention is an implant having a valve with a primary and secondary closure combination. The primary closure includes a diaphragm resiliently biased against an annular valve seat, with the diaphragm being opened and closed by the insertion and retraction of a filling tube, and with the diaphragm opening and closing in the axial direction of the valve, where the axial direction is defined by the filling tube. The secondary closure includes a pair of flaps opening and closing in a direction transverse to the axial direction.

Another feature of the present invention is the secondary closure itself. This closure includes a slit defined by a pair of opposing faces. To minimize the slit tearing at its ends and tearing into other parts of the valve or into the envelope itself, end portions of the faces are bonded to each other such that the slit generally has three portions running in line with each other: a first slit portion which is closed by adhesive, a second slit portion which is open, and a third slit portion which is closed by adhesive.

Another feature of the present invention is a two piece construction to the valve. One piece includes the secondary closure and one-half (the valve seat) of the primary closure. The other piece includes the other half (the diaphragm) of the primary closure. When the pieces lock to each other, annular flanges interlock and the diaphragm is resiliently biased against the valve seat.

Another feature of the present invention is the combination of an implant having 1) a silicone envelope formed by the mandrel dipping process, 2) a single opening and a valve engaged at the single opening, and 3) a saline based fill material.

Another feature of the present invention is a duck bill shape or duck bill like shape to the secondary valve. The duck bill like shape is provided to flaps that open and close, and the flaps have faces that are disposed at an angle relative to each other. Pressure applied to these faces draws the inner sealing edges of the flaps toward each other to even more tightly seal the secondary closure.

Another feature of the present invention is a guide for the tip of the filling tube. The guide is provided by a concave recess formed in the outer face of the flaps, and the flaps maintain a relative great thickness by virtue of the inner faces of the flaps extending inwardly (toward the inside of the implant) as the flaps extend toward each other.

Another feature of the present invention is a method for making the implant. Steps for making the implant including making an envelope with a single opening, engaging a valve at the single opening, and filling the envelope with a saline based fill material. Further unique steps include making the valve out of two pieces that mechanically interlock, and bonding portions of the secondary closure shut to minimize ripping of the valve or envelope.

An advantage of the present invention is a simple implant. The valve is simple to manufacture, simple to store and ship, simple to communicate to the surgeon how to implant and inflate and simple to reinflate.

Another advantage of the present invention is an implant with a minimum number of parts. In one embodiment, the implant as a whole has only three pieces:

a) the envelope (implant piece number one); and
b) the valve which has:
  i) the "first piece" (implant piece number two) having one-half of the primary closure; and
  ii) the "second piece" (implant piece number three) having the other half of the primary closure and all of the secondary closure. In another embodiment, the implant as a whole has only four pieces, with implant piece number four being one-half of the flap structure. In this embodiment, the flap structure is not molded as one piece. Instead, one half of the flap structure is bonded into place so as to provide an efficient method for forming the structure described above, i.e., a secondary closure having a first end slit portion which is bonded shut, a second middle slit portion which is open for insertion of the filling tube, and a third end slit portion which is bonded shut.

Another advantage of the present invention is an efficient use of the envelope. The envelope is used in generally the form it comes off the mandrel. This form has a single opening (formed by a support rod for the mandrel), and this single opening is used as the port for the introduction of fluid. The single opening is covered with the valve structure such that no cutting of the envelope to form other ports is required so as to maintain the integrity of the envelope. The least number of openings for an implant to be filled with a fill material is reasonably believed to be one, and this implant has preferably only one opening. Every opening or valve in an implant may potentially leak. The chance of leakage is reduced by reducing the number of openings.

DETAILED DESCRIPTION OF THE PREFERRED EMBODIMENTS

Figure 1A:
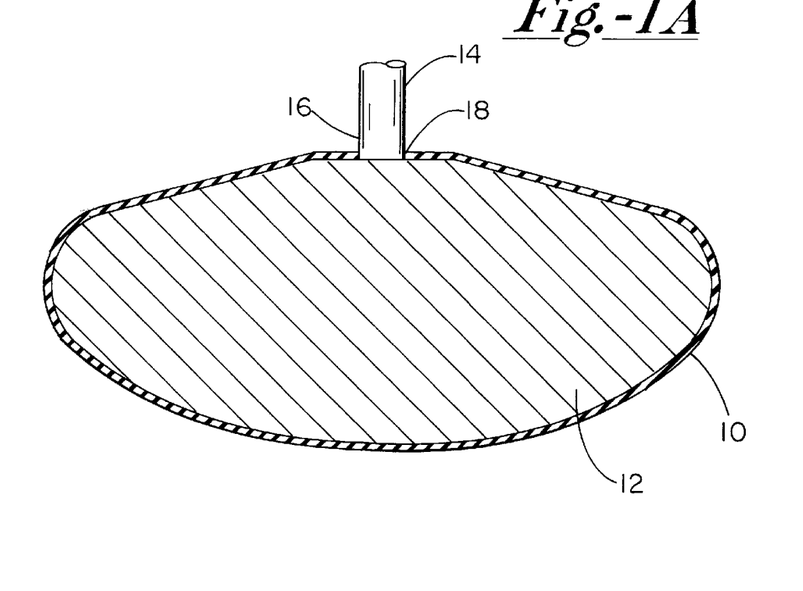
FIG. 1A shows a cross section of a mandrel and its centrally located support rod, and further shows the mandrel having an envelope being formed thereon by the mandrel being dipped a number of times into a silicone rubber dispersion.

FIG. 1 shows a silicone rubber envelope 10 of the present invention prepared by dip or solvent casting. The silicone rubber envelope 10 is formed on a mandrel 12 that is dipped several times or more into a dimethylsiloxane solution or dispersion. The mandrel 12 includes a centrally located support rod 14 having a threaded end 16 that is screwable onto and off the mandrel 12.

The mandrel 12 is completely submerged into the dimethylsiloxane solution or dispersion such that at least the threaded end 16 of the rod 14 is also submerged into the solution or dispersion. The mandrel 12 is then raised out of the solution or dispersion with a thin coating of the solution or dispersion on the mandrel 12. The thin coating is permitted to dry or at least partially dry (i.e. the solvent evaporates or is caused to evaporate by heat or blowers) and the dipping is repeated. The thin coatings or layers, when the desired thickness is attained, adhere to each other to essentially form a one layer integral envelope 10.

More specifically, the solution or dispersion for such a method preferably includes an elastomer such as dimethylsiloxane and a solvent such as xylene. The envelope 10 can be prepared from a two part silicone elastomer (available from Applied Silicone Corporation of Ventura, Calif., part no. 40,000 which includes the elastomer and cross-linking agent) in xylenes (26% w/w). The mandrel 12 is dipped into the dimethylsiloxane solution, withdrawn, and permitted to set at 130 degree F. (54.4 degrees C.), and then again dipped into the dimethylsiloxane solution, withdrawn, and permitted to set at 130 degree F. (54.4 degrees C.). If desired, the dipping, withdrawing and setting steps may be repeated a third time or more. As to dip or solvent casting, the Dogan et al. U.S. Pat. No. 5,630,844 issued May 20, 1997 is hereby incorporated by reference in its entirety.

The envelope or shell 10 is preferably formed by dip or solvent casting. However, formation of the shell or envelope 10 is not limited to the preferred method of solvent or dip casting. Other methods for forming an integral envelope or shell 10 include spray coating, injection molding, compression molding or blow molding.

Prior to or after the envelope 10 has dried, or during the drying and setting of the silicone elastomer of the envelope 10, a roughened texture 19 (shown in FIG. 4B) is applied to the exterior surface of the envelope 10 to minimize the chance of capsular contracture. The roughened texture 19 may be formed by ablating the exterior of the envelope 10 with sodium chloride. As to applying the roughened surface, the Dogan et al. U.S. Pat. No. 5,630,844 issued May 20, 1997 and the Ersek et al. U.S. Pat. No. 4,955,909 issued Sep. 11, 1990 are hereby incorporated by reference in their entireties.

Figure 1B:
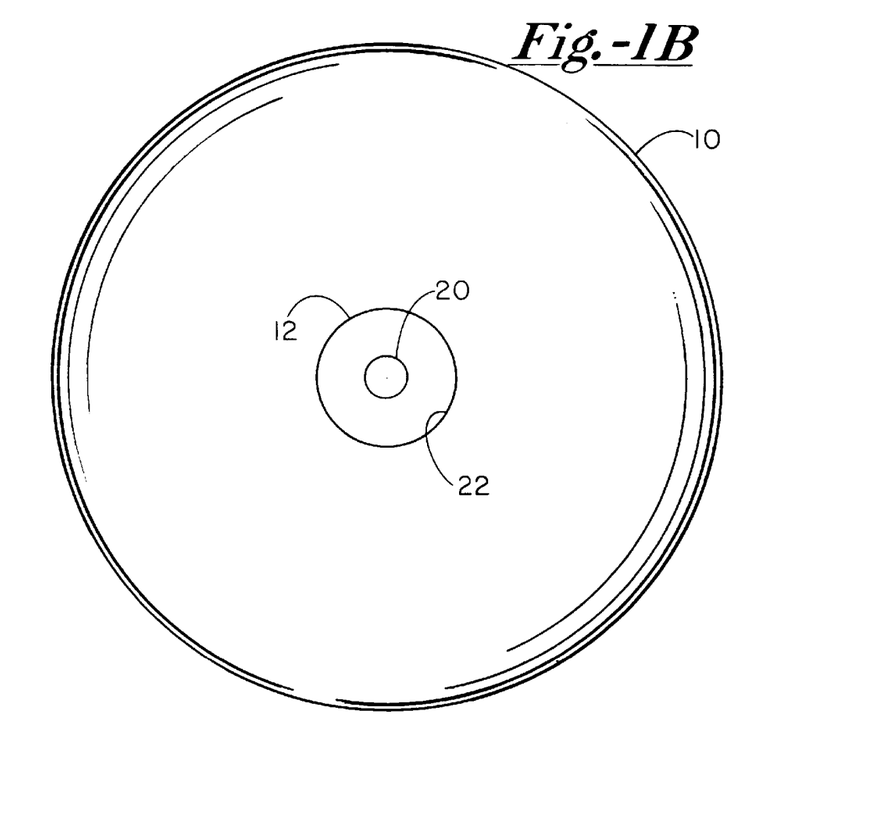
FIG. 1B shows a top view of the mandrel and envelope of FIG. 1A after the mandrel has been removed from its centrally located support rod, and shows the opening naturally formed by the centrally located support rod after the opening has been trimmed.

The dip or solvent casting method naturally forms a rough opening 18 (after the envelope has been fully dried) about the threaded end 16 of the mandrel rod 14. This rough opening 18 is trimmed by a tube like cutting tool having an annular cutting edge. The annular cutting edge is pressed about the rough opening 18 after the mandrel rod 14 has been screwed out of the threaded hole 20 of the mandrel 12 to remove a ragged piece of silicone elastomer having the rough opening 18. Such a trimming process leaves a trimmed circular opening 22 in the envelope 10. The elastomeric envelope 10 is then stretched such that the opening 22 is widened to the width of the mandrel 12, and the envelope 10 is then slipped off the mandrel 12.

Figure 2A:
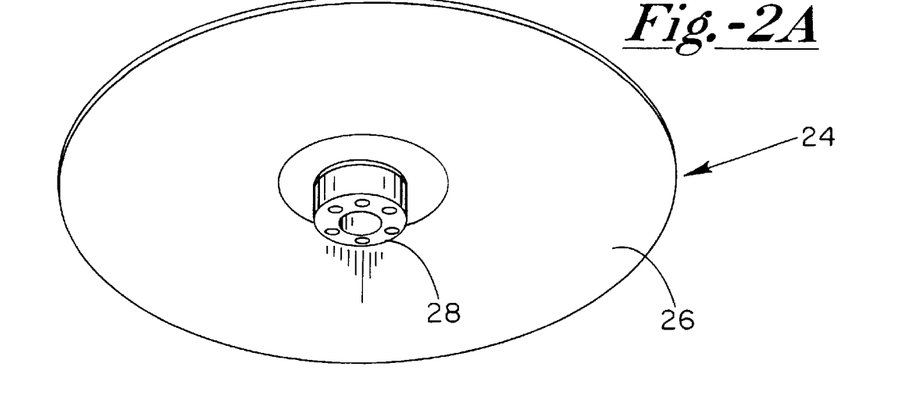
FIG. 2A shows a bottom (interior) perspective view of the valve structure that seals the opening of FIG. 1B.
Figures 2B, 2C:
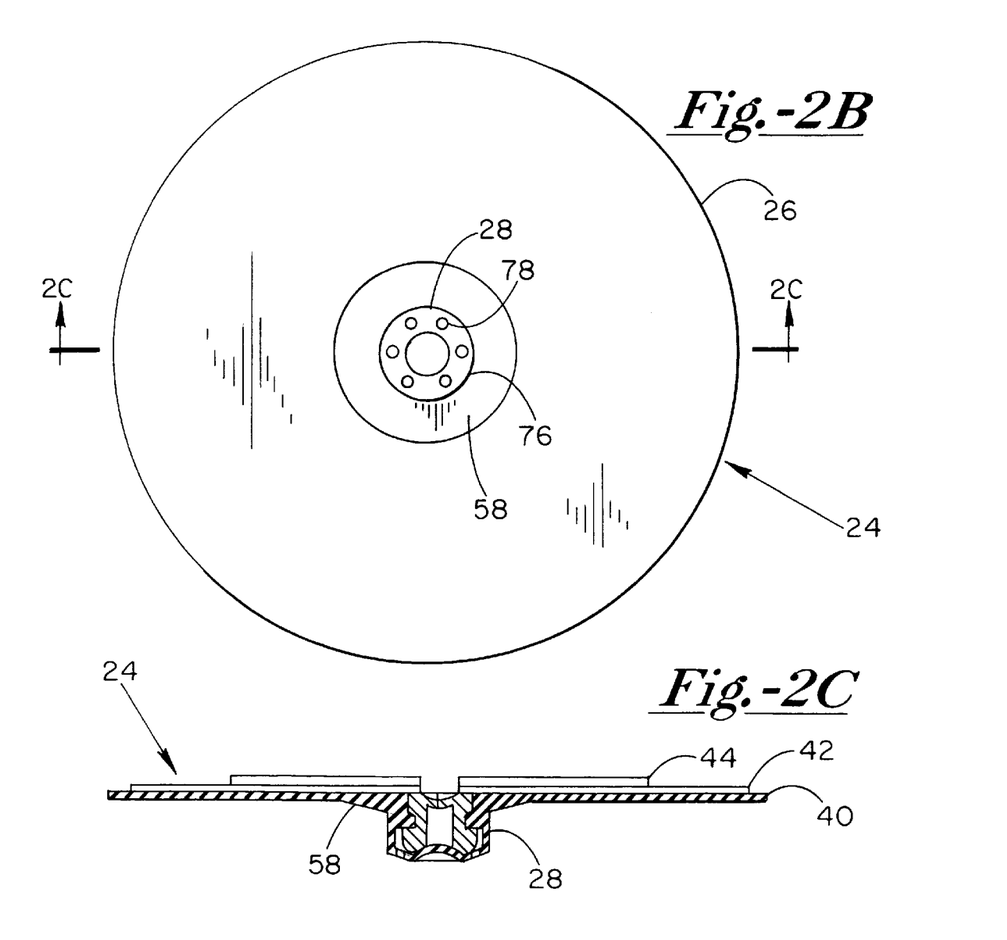
FIG. 2B shows a bottom (interior) view of the valve structure of FIG. 2A.
FIG. 2C shows a section view of the valve structure at lines 2C—2C of FIG. 2B.
Figure 3A:
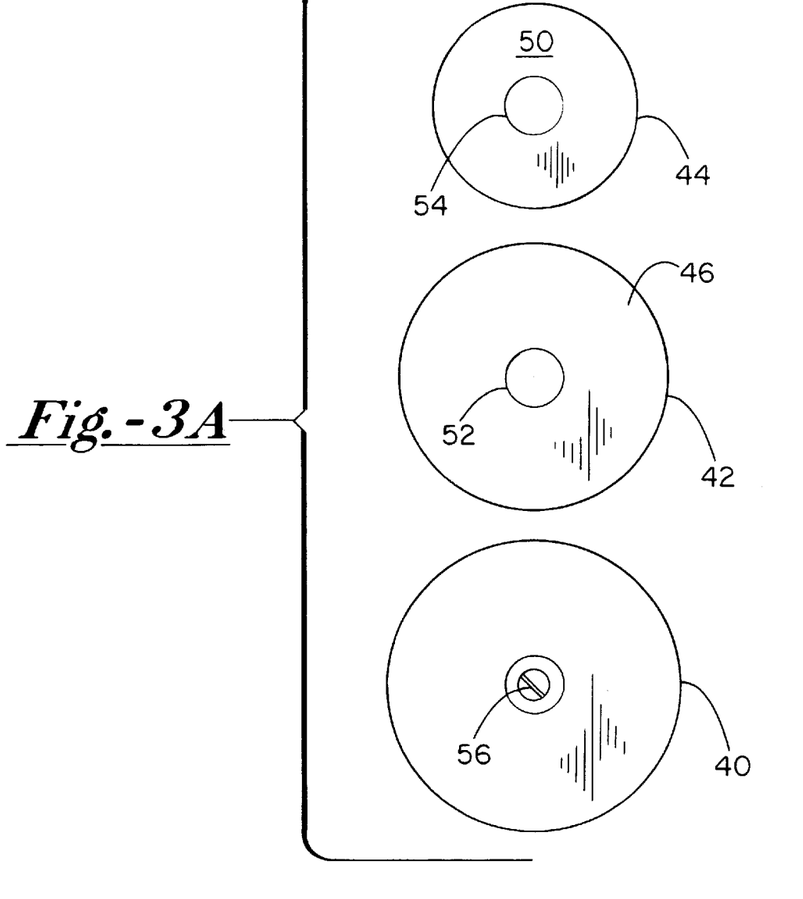
FIG. 3A shows top views of the vulcanized and unvulcanized base pieces for the valve structure of FIG. 2A.
Figure 3B:
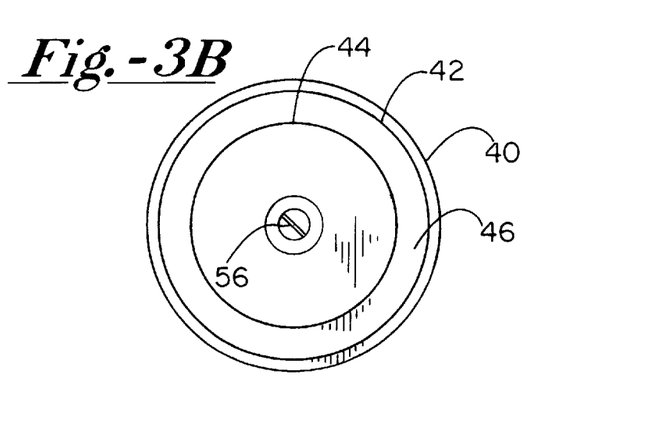
FIG. 3B shows a top view of the valve structure of FIG. 2A after the base pieces have been stuck together, but prior to being vulcanized.

FIGS. 2A, 2B and 2C show the valve structure 24 that is engaged to the envelope 10 over the opening 22. The valve structure 24 generally includes a valve base 26 and a valve 28.

As shown in FIGS. 2C, 3A, 3B and 3C, the valve base 26 includes an innermost vulcanized base layer portion 40, a middle unvulcanized base layer portion 42 and an outermost vulcanized base layer portion 44. The innermost base layer portion 40 includes an interior surface which makes contact with the fill material in the envelope 10. The innermost base layer portion 40 includes a diameter greater than the diameter of the trimmed hole 22.

The middle unvulcanized base layer portion 42 also includes a diameter greater than the diameter of the hole 22. The diameter of the middle unvulcanized base layer portion 42 is slightly less than the diameter of the innermost base layer portion 40 because, during vulcanizing, the unvulcanized layer 42 tends to expand or flow. An excessive expansion or flow may run beyond the edge of base layer portion 40 and cause inner opposing surfaces of the envelope 10 to bond to each other during a heating and pressing step (please see FIG. 5). The middle unvulcanized base layer portion 42 includes an upper annular surface portion 46 that confronts the interior surface 48 of the envelope 10 when the valve structure 24 is vulcanized to the envelope 10.

The outermost vulcanized base layer portion 44 includes a diameter substantially equal to the diameter of the opening 22. The outermost vulcanized layer 44 includes an exterior surface 50 that comes into contact with body tissue. The exterior surface 50 may include indicia such as product and company name and/or may include the roughened surface texture 19.

Middle unvulcanized portion 42 includes an opening 52 and outermost vulcanized portion 44 includes an opening 54 that are aligned with each other and further aligned with a valve opening or slit 56.

It should be noted that innermost portion 40 includes a thickened, tapering, annular portion or collar 58 that tapers from the valve 28 towards the circumference of the valve base 26. This collar 58 lends support to the connection between the portion of the valve 28 that has been molded with the outermost portion 40.

Figure 5:
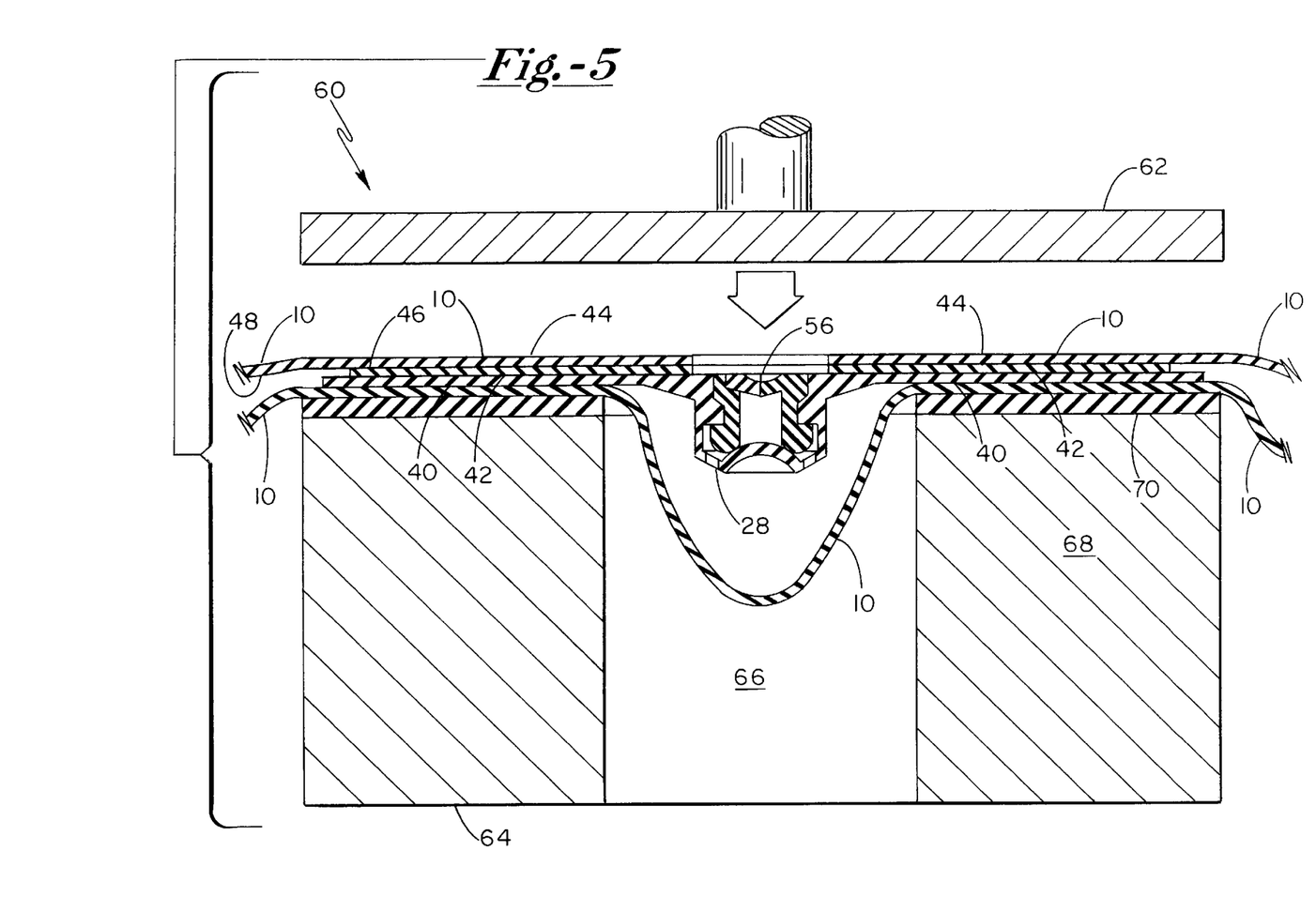
FIG. 5 is a section view of the valve structure and envelope of the present invention being pressed and heat treated so as to seal the valve structure in the envelope.

A pressing mechanism 60 to connect the valve structure 24 to the envelope 10 is shown in FIG. 5. The pressing mechanism 60 includes a press arm 62 and a base 64. Press arm 62 is disk like in shape and may be a pneumatic, hand operated screw or over center press. Base 64 is annular in shape and includes a central opening 66 for receiving the valve 28 in an out-of-the-way position when the press arm 62 confronts the base 64. Base 64 includes an aluminum portion 68 and a silicone portion 70 such that a like material makes contact with the material of the article that is being pressed. Press arm 62 may also include a surface layer of silicone on its pressing surface. The base press arm 62 and/or base 64 are heated to 350 degrees F. and the base 26 and the portion of the envelope 10 about the opening 22 are then pinched between the arm 62 and base 64 for two minutes to vulcanize the middle base portion 42 and thereby bond the middle base portion 42 to the innermost base portion 40, to the outermost base portion 44 and to the envelope 10.

Figure 6A:
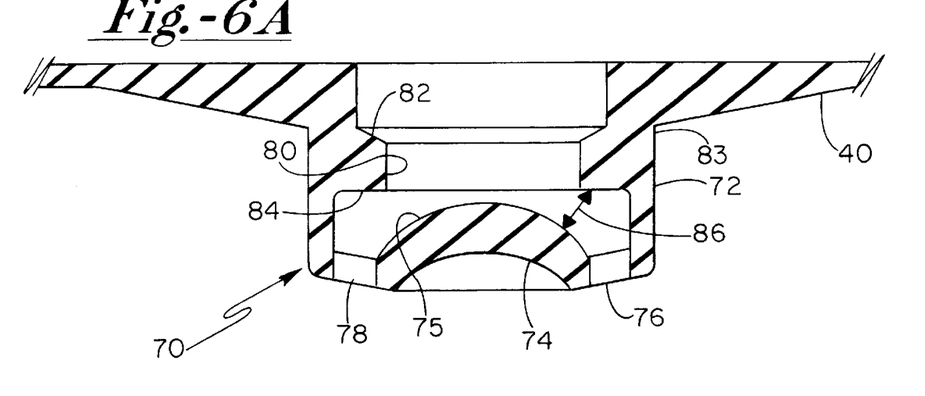
FIG. 6A is a detail section view of the valve of the valve structure of FIG. 2A, prior to assembly of the valve.

A first piece 70 of valve 28 is shown in detail in FIG. 6A. The first piece 70 includes the integral base layer portion 40 which is resilient, an annular resilient wall 72 integral with the base layer portion 40, and a resilient concave diaphragm 74 integral with the annular wall 72 and base layer portion 40. Diaphragm 74 includes a sealing face 75. Between the circumference of the diaphragm 74 and the annular wall 72 is a perforated resilient inwardly extending lip 76 having outlets 78 through which fill material flows into the envelope 10.

The annular wall 72 includes an inwardly extending annular locking flange 80. Flange 80 includes an face 82 which is oblique relative to an outer cylindrical face 83 of the annular wall 72, and an annular locking face 84 which is at generally a right angle to wall face 83. Oblique face 82 extends inwardly toward the diaphragm 74 and interior of the envelope 10. Reference arrow 86 indicates a relatively short distance between the sealing face 75 of diaphragm 74 and the locking flange 80.

It should be noted that the inner face of the collar 58 terminates at the foot of the outer cylindrical face 83. At such a location, oblique face 82 is beginning to form the annular locking flange 80. The collar 58 thereby provides greater support for the annular locking flange 80 and the valve 28 as a whole. In other words, the thickness or the degree of thickness of the collar 58 at its innermost portion continues to run into the annular locking flange 80 to provide support for the locking flange 80 and to in turn provide support for locking flange 96 of second piece 88 of valve 28.

It should be noted that the first piece 70 also includes, after valve structure or patch 24 is bonded to envelope 10, the middle base layer portion 42 and the outermost base layer portion 44. Such layer portions 40, 42 and 44 are effectively one layer after vulcanization.

A second piece 88 of valve 28 is shown in detail in FIGS. 6B, 6C, 7A, 7B, 7C and 7D. The second piece 88 includes an annular valve seat 90 for the diaphragm 74. In combination, the valve seat 90 and diaphragm 74 form a primary closure for the valve 28 to seal the outlets 78. The second piece 88 further includes a secondary closure 92 that minimizes or eliminates tissue ingrowth that otherwise may interfere with the sealing action of the primary closure.

Figure 6B:
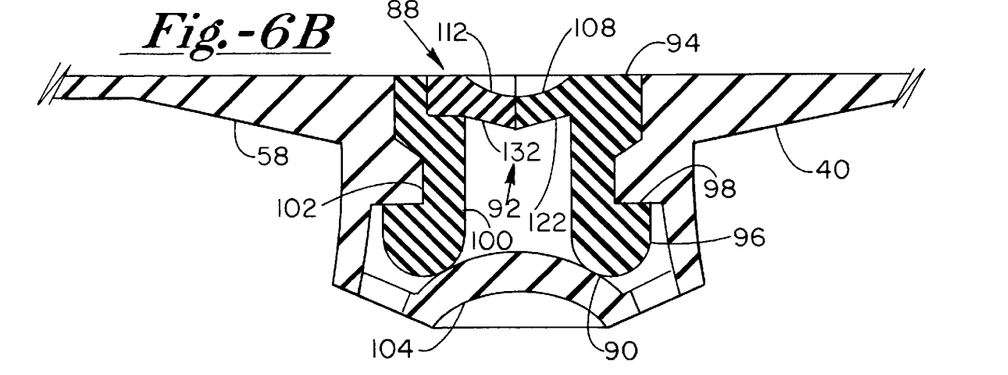
FIG. 6B is a view similar to FIG. 6A and shows a section view of the valve after assembly of the valve.

The second piece 88 is formed in the nature of a hollowed out plug or cylinder, with one end of the hollowed out cylinder sealed by the secondary closure 92. Conversely, the annular wall 72 of the first piece 70 is formed in the nature of a hollowed cylinder, with one end of the hollowed out cylinder sealed by the diaphragm 74 (in combination with the valve seat 90).

More specifically, second piece 88 includes an annular wall 94. The distal end of wall 94 includes the valve seat 90 with its curved sealing face. The distal end of wall 94 further includes an annular barb like outwardly extending locking flange 96. Flange 96 includes a face 98 that extends at a right angle to an interior cylindrical face 100 of the second piece 88. Face 98 and flange 96 of second piece 88 locks over face 84 and flange 80 of first piece 70 to lock the first and second pieces 70 and 88 together mechanically.

Prior to inserting the second piece 88 into the first piece 70, portions of the exterior of annular wall 94 may be coated with an adhesive, such as a silicone adhesive, to adhesively secure the pieces 70 and 88 together such that the pieces 70 and 88 are both mechanically and adhesively engaged to each other. When the second piece 88 is inserted into the first piece 70, the curved sealing face of the annular valve seat 90 slides over the annular oblique wall 82 of the first piece 70 so as to pinch or squeeze the resilient second piece 88 and so as to slightly expand the resilient first piece 70. Then the annular valve seat 90 of the locking flange 96 brings pressure to bear on the sealing face 75 of the diaphragm 74 and pushes the diaphragm 74 away from the flange 80 of the first piece 70. Then the locking flange 96 pops outwardly as its flange face 98 slides past flange face 84 of flange 80. At the same time flange 80 pops into an annular receptor 102 formed in annular wall 94 of the second piece 88 in the shape of the locking flange 80 of the first piece 70. When the pieces 70 and 88 are locked in place, the distance defined by arrow 86 is relatively great, with the locking flange 96 having pushed the diaphragm 75 into a resiliently biased position against valve seat 90 such that the outlets 76 are sealed. Further, pressure such as from fill material in the envelope 10 against a concave face 104 of the diaphragm 74 brings even a greater pressure to bear on the annular valve seat 90 and a greater sealing action between the diaphragm 74 and annular valve seat 90. Concave diaphragm face 104 is opposite of sealing diaphragm face 75.

As shown in FIGS. 7A–D, 8A–E and 9A–F, the secondary closure 92 is a flap structure that includes a first flap base 106 and a first flap 108 integrally extending from the first flap base 106 and that further includes a second flap base 110 and a second flap 112. First flap base 106 forms an end portion of annular wall 94 and extends circumferentially about flap 108. First flap base 106 includes a pair of end faces or slit forming faces 114 and 116 extending in the axial direction of tube like second piece 88. Flap 108 includes a concave outer surface 118 and a slit forming face or sealing face 120. Sealing face 120 extends in the axial direction of tube like second piece 88 and is coextensive with end faces 114 and 116 of flap base 106. Flap 108 further includes an inner face 122.

Second flap base 110 and second flap 112 is preferably initially molded as a separate piece from second piece 88. Second flap base 110 and second flap 112 are identical in shape to first flap base 106 and first flap 108 such that second flap base 110 extends circumferentially about flap 108, such that second flap base 110 includes a pair of end faces or slit forming faces 124 and 126 extending in the axial direction of tube like second piece 88 when the second flap base 110 and second flap 112 are glued into the second piece 88, such that second flap 112 includes a concave outer surface 128 and a slit forming face or sealing face 130, such that sealing face 130 extends in the axial direction of tube like second piece 88 and is coextensive with end faces 124 and 126, and such that second flap 112 includes an inner face 132. Further, it should be noted that second flap base 110 includes an annular base 134 that rides on and is glued to an annular base portion 133 of annular wall 94. Second flap base 110 further includes an annular side wall 135 that is glued to an annular inner sidewall portion 137 of annular wall 94.

As shown in FIGS. 8A, 8B, 8C, 8D and 8E, it should be noted that inner face 132 extends obliquely inwardly from the annular base 134 and that second flap 112 includes a side face portion 136 that tapers from the sealing face 130 to an intersection 138 between the inner face 132 and the base 134. It should be noted that the first flap 108 includes these same features such that the inner features of the flaps 108 and 112 provide a general duck bill shape to the secondary closure 92.

Figure 6C:
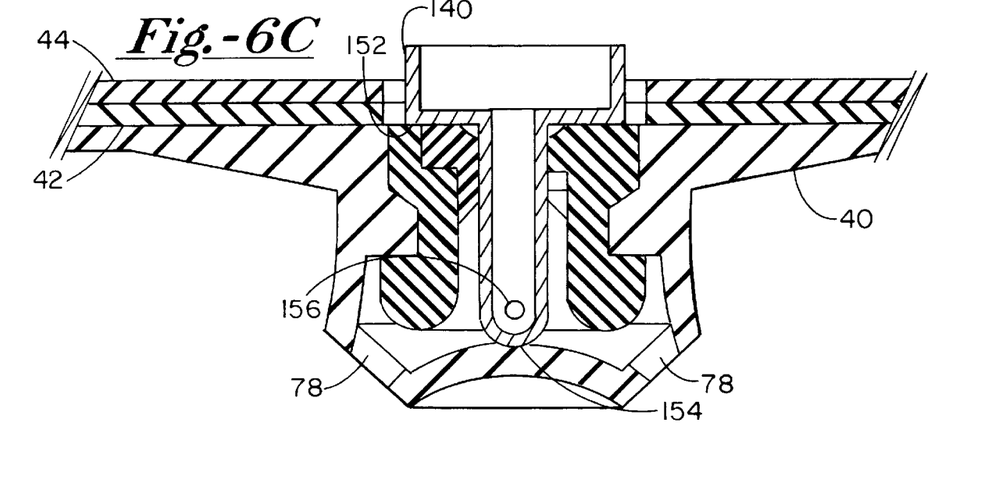
FIG. 6C is a view similar to FIG. 6A and shows a section view of the valve with an inflation tube or filling tube in the valve.
Figure 7A:
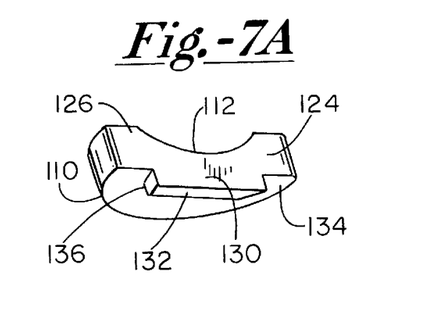
FIG. 7A is a perspective view of one flap and flap base for the valve of FIG. 6B.
Figure 7B:
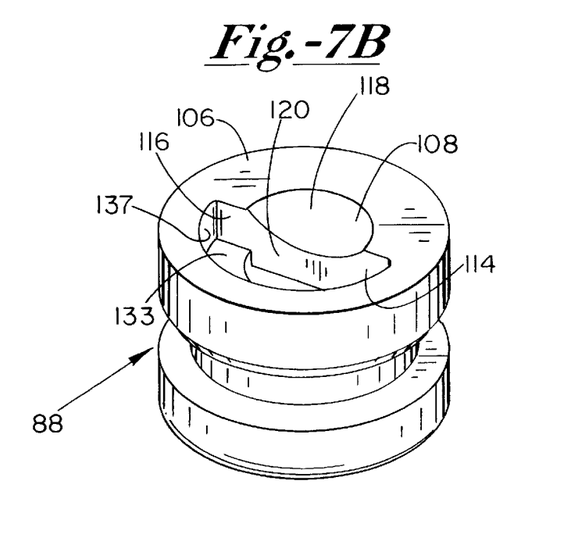
FIG. 7B is a perspective view of one portion of the valve of FIG. 6B without the flap and flap base of FIG. 7A.
Figure 7C:
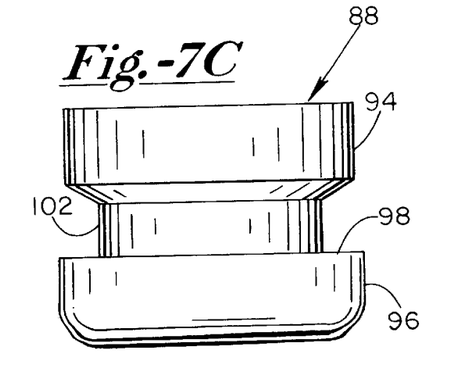
FIG. 7C shows a side elevation view of the portion of the valve of FIG. 6B.
Figure 7D:
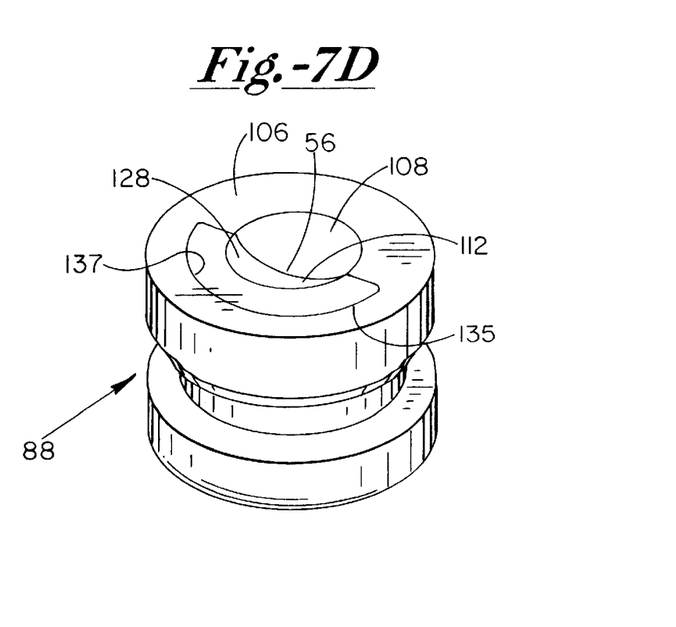
FIG. 7D is a perspective view of the portion of the valve shown in FIG. 7B after the flap and flap base of FIG. 7A has been bonded therein.
Figure 8A:
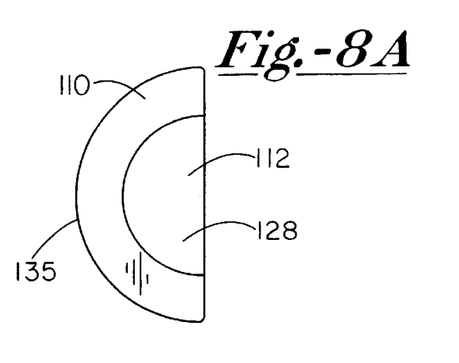
FIG. 8A shows a top view of the flap and flap base of FIG. 7A.
Figure 8B:
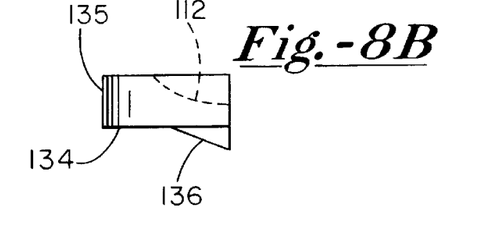
FIG. 8B shows a side, partially phantom view of the flap and flap base of FIG. 7A.
Figure 8C:
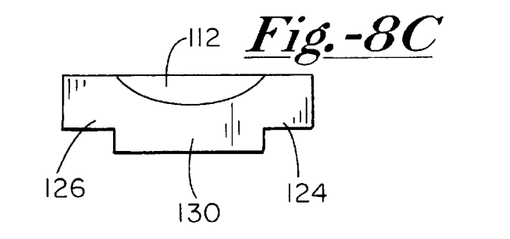
FIG. 8C shows an end view of the flap and flap base of FIG. 7A.
Figures 8D, 8E:
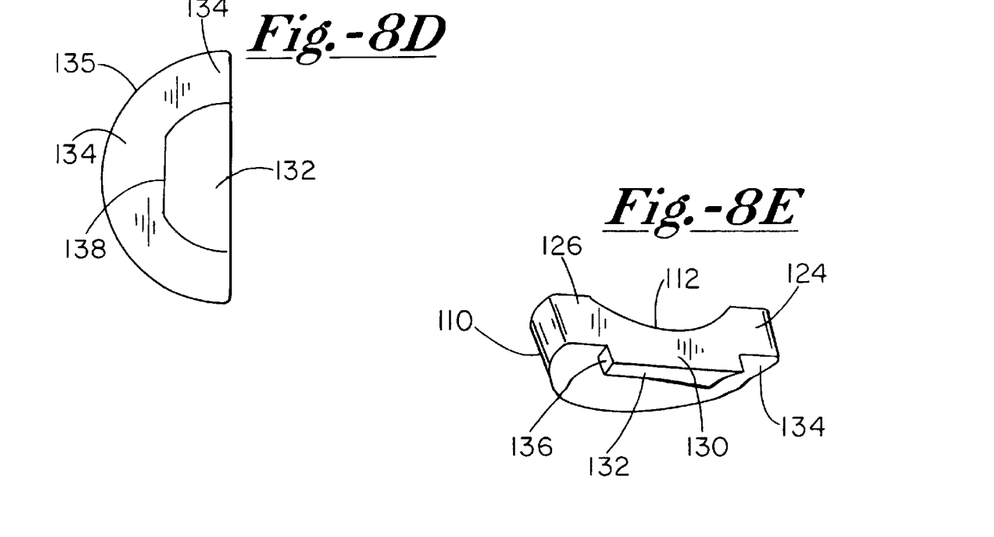
FIG. 8D shows a bottom view of the flap and flap base of FIG. 7A.
FIG. 8E is a perspective view of the flap and flap base of FIGS. 8A, 8B, 8C and 8D.

In combination, concave faces 118 and 128 form a concave guide for the insertion of a fill material tube or filling tube 140, shown in FIG. 6C. Opposite of the concave faces 118 and 128 are the inner flap faces 122 and 132, which extend inwardly so as to maintain a desired thickness to the flaps 108 and 112.

When second flap base 110 is glued to second piece 88, slit forming face 124 of the second base 110 is glued to slit forming face 116 of the first flap base 106. Likewise, slit forming face 126 of the second base 110 is glued to the slit forming face 114 of the first flap base 106. Accordingly, slit 56 includes a first end slit portion adhesively closed shut, a middle second slit portion formed by flap faces 120 and 130 pressing resiliently against each other, and a third end slit portion adhesively closed shut. By adhesively bonding the end portions of the slit 56 closed, the chance of tearing the second piece 88 is minimized when the filling tube 140 is inserted into the middle portion of the slit 56.

Figures 9A, 9B:
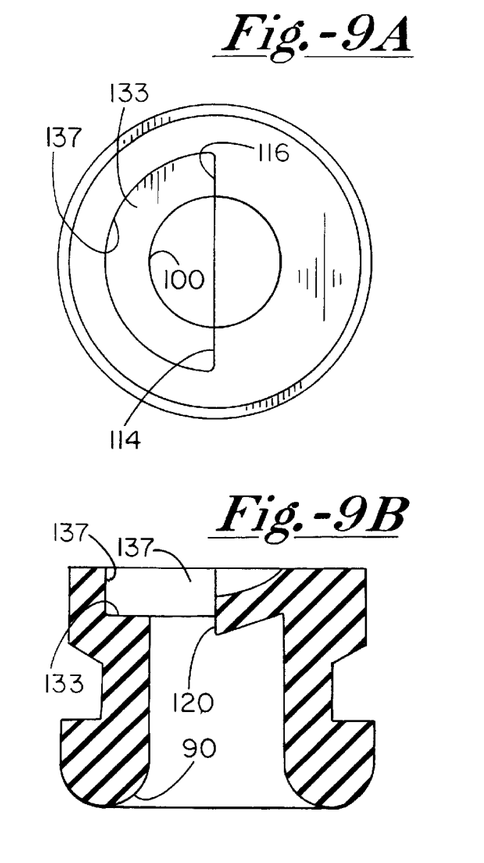
FIG. 9A is a top view of the valve portion of FIG. 7B.
FIG. 9B is a section view of the valve portion of FIG. 9A.
Figure 9C:
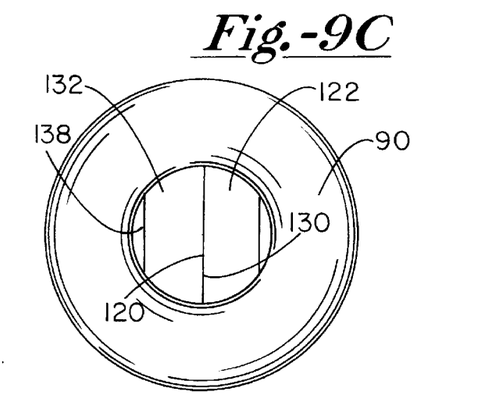
FIG. 9C is a bottom view of the valve portion of FIG. 9A.
Figures 9D, 9E:
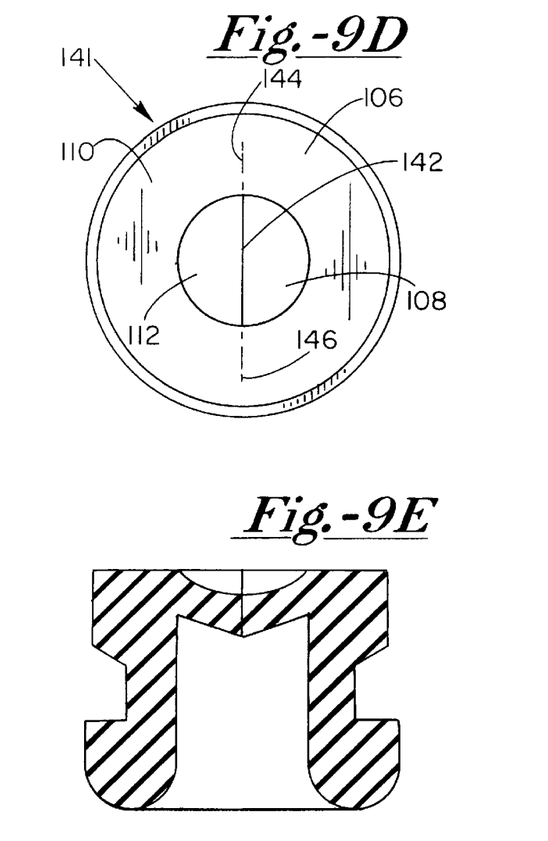
FIG. 9D is a top view of an alternate embodiment of the valve where both flap bases and flaps are integrally molded with the valve.
FIG. 9E is a section view of the integral valve embodiment of FIG. 9D.
Figure 9F:
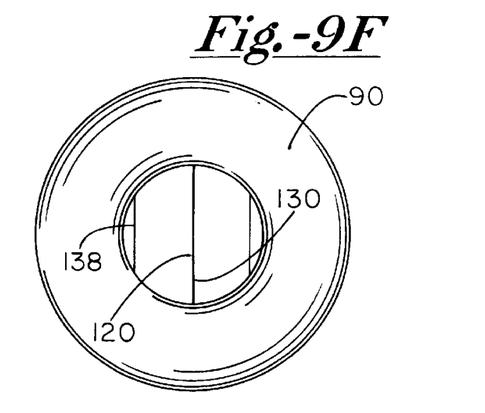
FIG. 9F is a bottom view of the integral valve embodiment of FIG. 9D.

FIGS. 9D, 9E and 9F show an alternate embodiment 141 of the second piece where the second flap base 110 and second flap 112 are molded integrally with the second piece 88 so as to form a slit 142 having no adhesively closed end portions. However, if desired, slit 142 may be extended on each end by cutting into the bases 106, 110 so as to form slit extensions 144 and 146 (shown in phantom in FIG. 9D). The depth of the slit extensions 144 and 146 runs to the depth of base 133 of the preferred embodiment. Then the slit extensions 144 and 146 are bonded shut with adhesive such as a silicone adhesive.

It should be noted that first piece 70, second piece 88 (including the second flap base 110 and second flap 112) are preferably formed of a resilient biocompatible plastic. More preferably, such a resilient plastic is a resilient silicone elastomer.

Figure 4A:
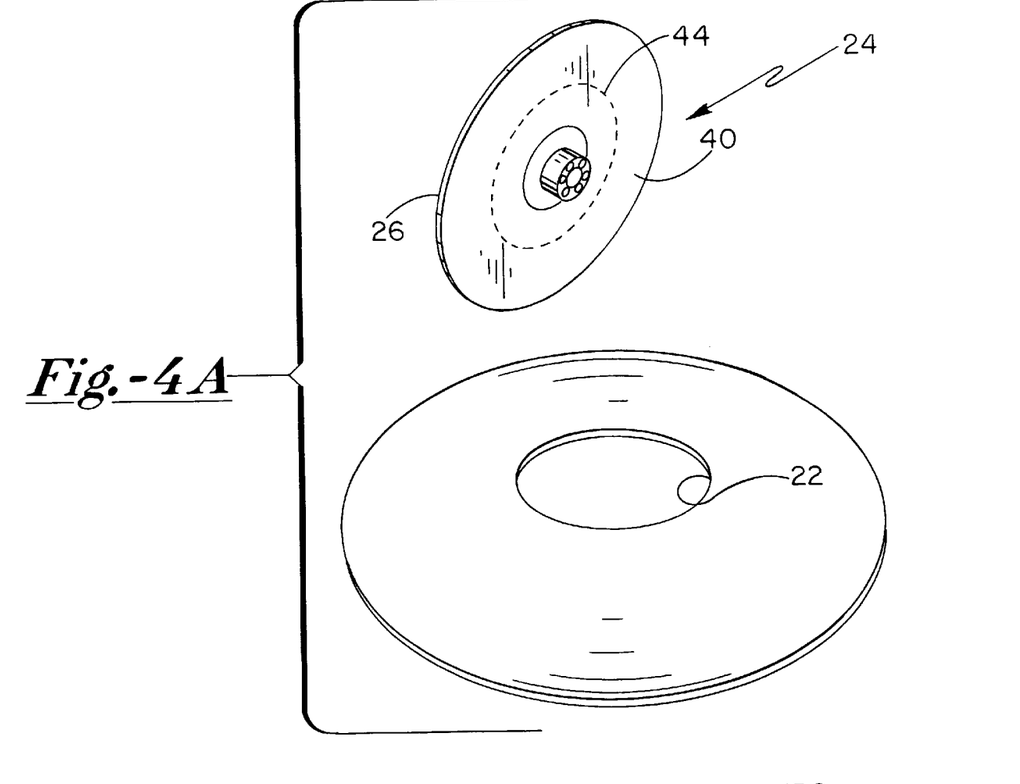
FIG. 4A shows an exploded view of the valve structure of FIG. 2A and envelope of 1B immediately prior to the valve structure being tucked inside the opening of the envelope.
Figure 4B:
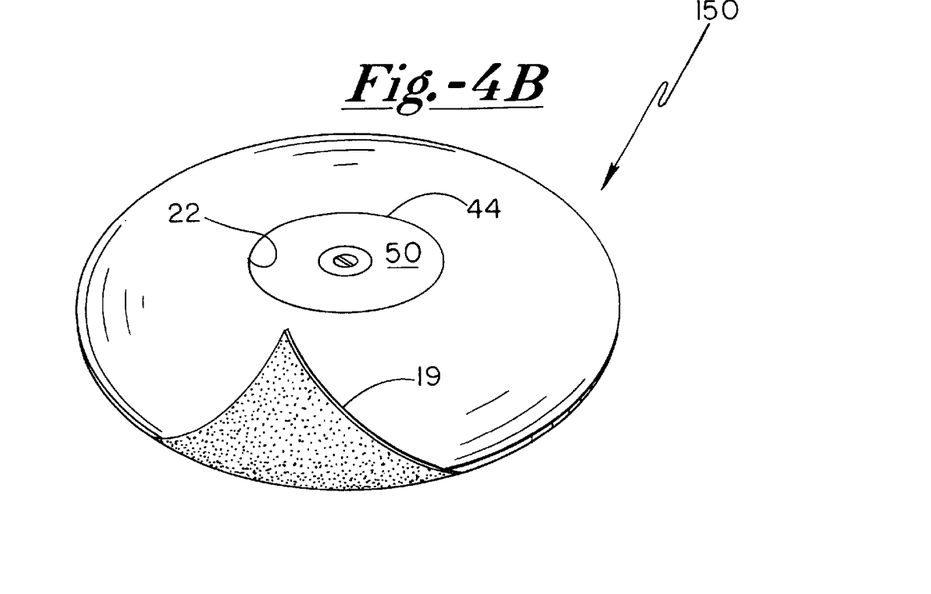
FIG. 4B shows a perspective view of the valve structure of FIG. 2A engaged in the envelope of FIG. 1A.

When assembled, the valve structure or patch 24 (which includes the first piece 70 and second piece 88, including the second flap base 110 and second flap 112) and envelope 10 in combination form an implant 150, shown in FIG. 4B. The implant 150 is preferably filled with a saline based fill material.

In operation, to fill the implant 150 with saline, the filling tube 140 is preferably used. The filling tube 140 includes an annular stop 152, a distal end 154 and an outlet 156. The distal end 154 is guided into the valve 28 by the concave faces 118 and 128, and the flaps 108 and 112 are pushed resiliently inwardly until the annular stop 152 engages the flap bases 106 and 110. The annular stop 152 is spaced a predefined distance from the distal end 154 so as to permit the filling tube 140 to be inserted a distance into valve 28 that is 1) sufficiently great so as to axially move diaphragm 74 out of a sealing relationship with valve seat 90 and 2) sufficiently small so as to minimize the chances of the diaphragm being punctured by the distal end 154. When the filling tube 140 pushes the diaphragm sealing face 75 away from the valve seat 90 and when the filling tube 140 is operated, fill material flows from the filling tube outlet 156, between the diaphragm sealing face 75 and valve seat 90, through the valve outlets 78 and into the interior of the implant 150. When the implant 150 is filled with the desired amount of fill material, the filling tube 140 is withdrawn. Diaphragm 74, which is resiliently biased toward valve seat 90, automatically closes and the flaps 108 and 112, which are resiliently biased outwardly and toward each other such that the sealing faces 120 and 130 resiliently press together, close automatically. Pressure from the fill material works outwardly against concave diaphragm face 104 to push the diaphragm sealing face 75 against valve seat 90. Further, the sealing faces 120 and 130 of the flaps 106 and 110 push resiliently against each other when closed.

It should be noted that the implant 150 as a whole, including the envelope 10 and the valve structure 24 with the valve base 26 and valve 28, is preferably formed of a biocompatible elastomer. Of biocompatible elastomers, a silicone elastomer is preferred.

It should be noted that the implant 150 as a whole, including the envelope 10 and the valve structure 24 with the valve base 26 and valve 28, is preferably generally transparent.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

What is claimed is:

1. An implant for the body, comprising, in combination:
 a) a resilient envelope;
 b) fill material in the envelope to provide a volume to the envelope; and
 c) a valve, with the valve being adapted to receive a tube for introducing fill material into the envelope, with the valve comprising:

i) a resilient primary closure for sealing the fill material in the envelope, with the primary closure being opened and closed when the tube is inserted into and withdrawn from the valve; and ii) a resilient secondary closure, with the secondary closure being opened and closed when the tube is inserted into and withdrawn from the valve, with the resilient secondary closure being disposed outwardly relative to the primary closure such that when the tube is inserted into the valve the tube first opens the secondary closure and then opens the primary closure and such that when the tube is withdrawn from the valve the primary closure closes first automatically and the secondary closure closes second automatically.

2. The implant according to claim 1 wherein the valve includes an axis having an axial direction, with the tube being inserted and withdrawn in the axial direction, with the primary closure comprising a diaphragm on the axis and a valve seat on the axis, with the diaphragm being opened and closed generally in the axial direction to open and sealingly close the valve, with the secondary closure comprising a resilient flap structure opening and sealingly closing in a direction transverse to the axial direction.

3. The implant according to claim 2 wherein the flap structure is integral with the valve.

4. The implant according to claim 2 wherein the flap structure comprises a pair of flap bases and flaps, with each of the flaps extending from one respective flap base, with the flap having an inner sealing edge that opens from and closes against the inner sealing edge of the other flap, with said flap base having two end edges and with said inner sealing edge running into and being integral with said two end edges of the base, with the two end edges of one of the flap bases being adhesively engaged to the two end edges of the other of the flap bases to strengthen an area where the flap opens and closes along the inner sealing edges to minimize chances of the valve splitting when the tube is inserted and withdrawn from the valve.

5. The implant according to claim 4 wherein one flap base and flap is a piece distinct from a remaining portion of the valve, with said one flap base and flap being engaged to said remaining portion of the valve.

6. The implant according to claim 5 wherein said one flap base and flap is engaged to said remaining portion of the valve with an adhesive.

7. The implant according to claim 2 wherein each of the flaps includes an inner sealing edge, wherein the inner edges resiliently sealingly engage each other to provide said secondary closure, and wherein each of the flaps includes an inner face, with each of the inner faces running inwardly into the implant and toward each other such that outwardly directed pressure applied onto the faces pushes the inner edges even more tightly together.

8. The implant according to claim 7, wherein the flaps as a whole include an outer surface, with the outer surface including a guide for the tube, with the guide being set in from an outer surface of the envelope, with the inner faces as a whole being disposed opposite of the guide.

9. The implant according to claim 2 wherein the flaps as a whole include an outer surface, with the outer surface being concave to serve as a guide for the tube.

10. The implant according to claim 1 wherein the valve comprises first and second distinct pieces, with the first piece comprising a diaphragm and with the second piece comprising a valve seat for the diaphragm.

11. The implant according to claim 10 wherein the first piece further comprises a first annular flange and wherein the second piece further comprises a second annular flange that locks over the first annular flange to mechanically lock the first and second pieces to each other.

12. The implant according to claim 11 wherein the first and second pieces are further engaged to each other with an adhesive.

13. The implant according to claim 11 and including a distance between the first annular flange and the diaphragm when the first piece stands alone, with said distance being increased when the second piece is locked to the first piece such that the diaphragm is resiliently biased against the valve seat.

14. The implant according to claim 1 wherein the fill material comprises saline and the envelope comprises no more than one opening, with the valve engaged at the opening.

15. The implant according to claim 1 wherein the secondary closure comprises first, second and third slits, with the first, second and third slits running into each other, with the first slit being disposed between the second and third slits, with the first slit being openable when the tube is inserted into the first slit, with the second and third slits being sealed with an adhesive to minimize the chances of the secondary closure being split open by an insertion and retraction of the tube into and from the first slit.

16. An implant for the body, comprising, in combination:

a) a resilient envelope;

b) fill material in the envelope to provide a volume to the envelope; and c) a valve, with the valve being adapted to receive a tube for introducing fill material into the envelope, with the valve comprising a pair of resilient flap bases and resilient flaps, with each of the flaps extending from one respective flap base, with the flap having an inner sealing edge that opens from and closes against the inner sealing edge of the other flap, with said flap base having two end edges and with said inner sealing edge running into and being integral with said two end edges of the base, with the two end edges of one of the flap bases being adhesively engaged to the two end edges of the other of the flap bases to strengthen an area where the flap opens and closes along the inner sealing edges to minimize chances of the valve splitting when the tube is inserted and withdrawn from the valve.

17. The implant according to claim 16 wherein the fill material comprises saline.

18. The implant according to claim 16 wherein each of the bases extends circumferentially about one respective flap.

19. An implant for the body, comprising, in combination:

a) a resilient envelope having no more than a single opening;

b) fill material in the envelope to provide a volume to the envelope, with the fill material comprising saline; and c) a valve engaged over the opening, with the valve being adapted to receive a tube for introducing fill material into the envelope, with the valve comprising first and second distinct pieces engaged together, with the first piece comprising a resilient diaphragm and a receptor for the second distinct piece, with the second piece engagable in the receptor and comprising a valve seat against which the diaphragm opens and closes such that the diaphragm and valve seat form a primary closure that opens and automatically closes when the tube is inserted into and withdrawn from the valve, and with the second piece comprising a resilient secondary closure, with the secondary closure being opened and automatically closed when the tube is inserted into and withdrawn from the valve, with the resilient secondary closure being disposed outwardly relative to the primary closure such that when the tube is inserted into the valve the tube first opens the secondary closure and then opens the primary closure.

20. The implant according to claim 19 wherein the first piece further comprises a first annular flange and wherein the second piece further comprises a second annular flange, with the second annular flange locking over the first annular flange to mechanically lock the first and second pieces to each other.

21. The implant according to claim 20 wherein the first piece is integral with the envelope, and further comprising a collar between the first piece and the envelope, with the collar tapering outwardly, with the collar leading into the first annular flange so as to provide strength to the first annular flange and support for the second annular flange.

* * * * *